United States Patent [19]

Dotson, Jr.

[11] 4,316,465

[45] Feb. 23, 1982

[54] OPHTHALMIC HANDPIECE WITH PNEUMATICALLY OPERATED CUTTER

[76] Inventor: Robert S. Dotson, Jr., 421 Warner Park Rd., Manhattan, Kans. 66442

[21] Appl. No.: 98,491

[22] Filed: Nov. 29, 1979

Related U.S. Application Data

[63] Continuation-in-part of Ser. No. 25,537, Mar. 30, 1979, Pat. No. 4,274,411.

[51] Int. Cl.³ .............................................. A61M 1/00
[52] U.S. Cl. .................................... 128/276; 128/305; 433/121
[58] Field of Search .................. 145/53; 433/120, 121, 433/128, 133, 118, 122, 123; 408/126, 124, 130, 137; 128/276, 277, 751, 752, 753, 754, 755, 305, 53

[56] References Cited

U.S. PATENT DOCUMENTS

| | | | |
|---|---|---|---|
| 2,708,437 | 5/1955 | Hutchins | 128/751 |
| 2,728,556 | 12/1955 | House | 145/53 |
| 3,042,041 | 7/1962 | Jascalevich | 128/276 |
| 3,589,363 | 6/1971 | Banko et al. | 128/276 |
| 3,682,166 | 8/1972 | Jacobs | 128/276 |
| 3,730,180 | 5/1973 | Davison | 128/204.24 |
| 3,734,099 | 5/1973 | Bonder et al. | 128/305 |
| 3,815,604 | 6/1974 | O'Malley et al. | 128/305 |
| 3,884,234 | 5/1975 | O'Malley et al. | 128/305 |
| 3,885,567 | 5/1975 | Ross | 128/278 |
| 3,900,022 | 8/1975 | Widram | 128/7 |
| 3,906,954 | 9/1975 | Baehr et al. | 128/305 |
| 3,932,065 | 1/1976 | Ginsberg et al. | 251/5 |
| 3,982,540 | 9/1976 | Ross | 128/278 |
| 4,016,882 | 4/1977 | Broadwin et al. | 128/305 |
| 4,041,947 | 8/1977 | Weiss et al. | 128/276 |
| 4,052,987 | 10/1977 | Wuchinich et al. | 128/276 |
| 4,061,146 | 12/1977 | Baehr et al. | 128/305 |
| 4,136,700 | 1/1979 | Broadwin et al. | 128/276 |
| 4,210,146 | 7/1980 | Banko | 128/305 |

FOREIGN PATENT DOCUMENTS

254223 12/1923 Fed. Rep. of Germany ...... 128/910
600781 7/1934 Fed. Rep. of Germany ...... 128/305

*Primary Examiner*—Robert W. Michell
*Assistant Examiner*—J. L. Kruter

[57] ABSTRACT

An ophthalmic handpiece is disclosed. The handpiece includes coaxial irrigation and aspiration needles, with passageways through the body of the handpiece for connection to conventional equipment for supplying irrigation and aspiration. Within the aspiration needle, there is a reciprocating cutting device for cutting tissue, that extends into the aspiration needle. The cutting device is moved by a driving device that rotates as it moves, to rotate the cutting device during the cutting motion. The aspiration passageway is also provided with a supply for reflux irrigation to assist in removal of tissue from the aspiration port.

5 Claims, 3 Drawing Figures

OPHTHALMIC HANDPIECE WITH PNEUMATICALLY OPERATED CUTTER

CROSS REFERENCE TO RELATED APPLICATION

This application is a continuation-in-part of the co-pending application of the same inventor titled "Fluid Operated Ophthalmic Irrigation and Aspiration Device," filed Mar. 30, 1979, under Ser. No. 25,537, now U.S. Pat. No. 4,274,411.

FIELD OF THE INVENTION

This invention relates generally to ophthalmic equipment, and is more particularly concerned with a handpiece for providing irrigation and aspiration, and including pneumatically operated cutting means.

BACKGROUND OF THE INVENTION

When a surgeon is to operate inside the eye of a patient, the presently used technique generally includes the insertion of a needle which provides for a supply of irrigation fluid as well as a passage for aspiration so that unwanted fluids and some solid matter can be aspirated from the eye. There are times when some tissue needs to be severed, and some prior art handpieces have been provided with cutting means in conjunction with the aspiration. The above identified co-pending application provides control circuitry whereby a pulsing pressure is provided to assist in cutting, but there are still times when the tissue is somewhat difficult to cut. Also, when aspiration is used within the eye, it sometimes happens that a piece of tissue inadvertently lodges within the aspiration port. If this tissue is not to be severed, it is sometimes quite difficult to remove the tissue from the aspiration port quickly and without causing trauma.

SUMMARY OF THE INVENTION

The present invention overcomes above mentioned and other difficulties with the prior art by providing an ophthalmic handpiece including one needle for providing irrigation fluid to the site, and a coaxially disposed needle for providing aspiration from the site, the needle for providing aspiration having cutting means internally thereof. Driving means for the cutting means also provides for rotation of the cutting means during the cutting operation. In the preferred embodiment of the invention, the driving means is pneumatically operated. A further feature of the invention is the provision for reflux irrigation through the aspiration port to assist in removal of tissue therefrom without trauma.

BRIEF DESCRIPTION OF THE DRAWINGS

These and other features and advantages of the present invention will become apparent from consideration of the following specification when taken in conjunction with the accompanying drawings in which.

DESCRIPTION OF THE PREFERRED EMBODIMENT

Figure 1:
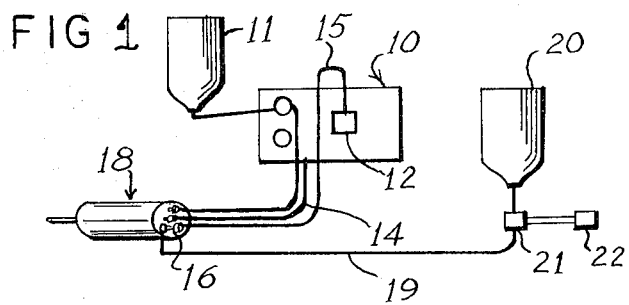
FIG. 1 is a schematic diagram showing an irrigation and aspiration device connected to a handpiece made in accordance with the present invention, and showing the supply for reflux irrigation.

Referring now more particularly to the drawings, and to that embodiment of the invention here presented by way of illustration, it will be seen in FIG. 1 that the irrigation and aspiration device is indicated at 10, the device including a liquid supply 11 and a source of vacuum at 12. These features are discussed and shown in detail in the above identified co-pending application which is incorporated herein be reference. It will be understood that the co-pending application includes a line such as the line 14 for providing pressure to operate a pneumatic cutter.

It will be seen in FIG. 1 of the drawings that the line 15 which leads from the source of vacuum 12 is connected to a Y adaptor 16 for providing aspiration through the handpiece 18, and the other side of the Y adaptor is connected to a tubing 19 which leads to a second liquid supply 20. As is here shown schematically, the tubing 19 includes a clamp 21 having a clamp operating means 22 to allow selective flow of liquid from the bottle 20 to the Y adaptor 16. This arrangement will be discussed in more detail hereinafter.

Figure 2:
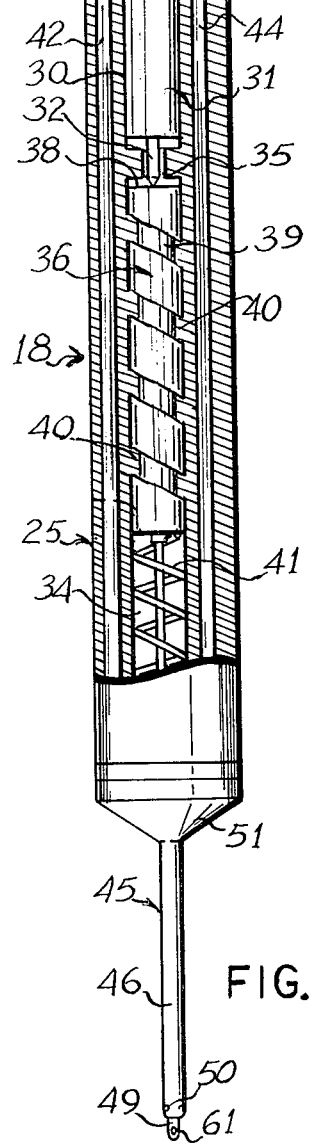
FIG. 2 is a side elevational view of the handpiece of the present invention, a portion thereof being shown in cross-section; and, FIG. 3 is a much enlarged, partial longitudinal cross-sectional view of the handpiece shown in FIGS. 1 and 2 of the drawings.

Attention is next directed primarily to FIG. 2 of the drawings for a general understanding of the handpiece of the present invention. It will be seen that the handpiece 18 includes a body 25 having a rear end plug 26 which has the tubing connectors formed integrally therewith. The tubing connector 16 is the Y adaptor shown in FIG. 1 of the drawing, and there is also a tubing connector 28 to receive the line 14 for operating the cutter which will be described in detail hereinafter. The next connector 29 is designed to receive the tubing from the standard irrigation bottle 11 for supplying irrigation fluid during the procedure.

The body 25 of the handpiece 18 is generally cylindrical, and is provided with a rear axial bore 30 for receiving a fluid actuated cylinder 31. Though the internal mechanism of the cylinder 31 is not here illustrated, it will be well understood by those skilled in the art that such a device would have a rod 32 projecting therefrom, the rod 32 being further projected from the cylinder 31 with the application of fluid pressure through the connector 28. On removal of the pressure from the connector 28 the rod 32 can be pushed back into cylinder 31. Various such devices are readily available, and no further description is thought to be necessary.

The body of the handpiece 18 is also provided with a forward bore 34. As is here shown, the bore 34 is approximately the same diameter as the bore 30, though it will be realized that dimensional changes can be made quite readily to accommodate the particular apparatus to be determined by appropriate engineering for a given handpiece. Between the bores 30 and 34, there is a connecting passage 35 through which the rod 32 extends.

Within the bore 34, it will be seen that there is a driving device 36. The driving device 36 is sized to be a slidable fit in the bore 34, and the rearmost end of the driving device 36 is contacted by the rod 32. As here shown, rod 32 has a pointed end for engaging the rearmost surface 38 of the driving device 36, the point being desirable to reduce the frictional drag to a minimum. Obviously bearings and other well known expedients may be used, but the arrangement here illustrated is simple and effective.

It will be observed that the driving device 36 has a helical groove 39 in the surface thereof; and, the bore 34 is provided with helical ridges 40 for cooperating with the groove 39. With this arrangement, it will be seen that, as the driving device 36 is reciprocated with the bore 34, the action of the ridges 40 within the grooves 39 will cause the driving device 36 to rotate about its axis.

Also, within the bore 34, and forwardly of the driving device 36, there is a coil spring 41 which engages the forwardmost end of the driving device 36. Thus, it will be understood that fluid pressure can be admitted through the connector 28 to cause the rod 32 to be extended from the cylinder 31, acting on the rear surface 38 of the driving device 36 to cause the driving device 36 to move forward. During the forward movement, the driving device 36 will rotate about its axis due to the interaction of the helical grooves 39 and the ridges 40. When the driving device 36 is at its forwardmost position, the fluid pressure can be removed from the connector 28 so that the spring 41 will urge the driving device 36 rearwardly, causing the rod 32 to be retracted into the cylinder 31.

It will also be noted in FIG. 1 that there is a passage 42 extending from the connector 29 and through the body 25. This passage 42 conducts the irrigation fluid from the connector 29 to the needle as will be discussed in detail later. On the opposite side of the body 25 as shown in FIG. 2, there is a passage 44 which is connected to the Y connector 16, primarily for the aspiration through the needle, which will be discussed in detail later.

Figure 3:
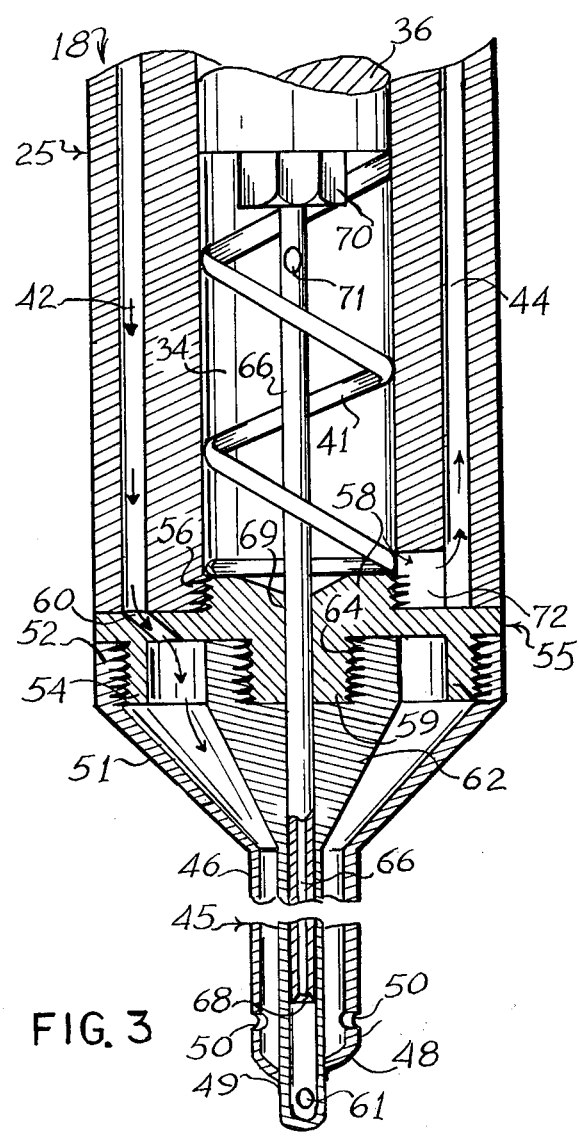

Attention is next directed to FIG. 3 of the drawing which discloses the construction of the forward end of the handpiece 18 in greater detail. Here it will be seen that the handpiece 18 has a needle generally indicated at 45, the needle 45 including an outer, irrigation needle 46 which turns inwardly at 48 to engage the aspiration needle 49. The irrigation needle 46 is provided with one or more irrigation openings 50 for delivery of irrigation fluid to the site of the procedure.

To connect the irrigation needle 46 to the body 25, the irrigation needle 46 flares outwardly at 51 so that the outside diameter of the needle 46 is approximately equal to the outside diameter of body 25. The annular flange 52 of the needle 46 is provided with internal threads 54 for engaging complementary threads on a transition fitting 55.

It will now be seen that the forwardmost end of the bore 34 is provided with threads 56 for threaded engagement with the extension 58 of the transition piece 55 so that the body 25 is attached to the transition piece 55. Similarly, threads 54 engage the threaded, annular extension 59 of the transition piece 55 to secure the needle 46 to the transition piece 55, hence to the body 25. It should further be noted that passageway 42 is aligned with a hole 60 through the transition piece 55 so that irrigation fluid can pass through the transition piece 55 and into the irrigation needle 46.

Within the irrigation needle 46 is the aspiration needle 49. It will be understood that the fit between the inturned portions 48 of the needle 46 and the needle 49 is sufficiently close that little or no irrigation fluid will leak from the juncture, and the aspiration port 61 is forward of the needle 46 so that the aspiration port 61 is outside the irrigation needle 46. The aspiration needle 49 extends axially of the irrigation needle 46 and is provided with an enlarged end 62 having internal threads 64 which mate with threads on an extension 59 of the transition piece 55.

Next, it will be seen that there is a cutting device 66 which has its cutting edge 68 adjacent to the aspiration ports 61. It will be understood that the cutting device 66 is movable forward, towards the aspiration port 61. When a piece of tissue extends into the aspiration needle 49 through the aspiration port 61, the cutting device 66 can be moved forwardly, past the aspiration port 61 to sever the tissue extending therethrough.

It will be seen that the cutting device 66 extends entirely through the aspiration needle 49, and through a central passageway 69 in the transition piece 55. The cutting device 66 extends further to be connected to the driving device 36. While many forms of connection may be devised, the cutting device 66 is here shown as being threadedly received within a nut 70 so that the cutting device 66 can be replaced if desired.

In order to achieve aspiration through the aspiration needle 49, it will be seen that the cutting device 66 is hollow, that is to say tubular, and is provided with an opening 71 so that the inside of the cutting device 66 can communicate with the bore 34. A port 72 is provided from the bore 34 to communicate with the passageway 44 which, as will be remembered, communicates with the Y-connector 16.

From the foregoing, the operation of the device should now be understood. The conventional equipment would be operated to supply the aspiration, or vacuum force, to the connector 16 to provide aspiration through the aspiration port 61 through aspiration needle 49, and through the center opening of the cutting member 66 and out the opening 71 into the bore 34. From the bore 34, aspiration is provided through the passageway 72 and through the passage 44 so long as the controls provide aspiration at the connector 16. Also, so long as the usual controls provide for irrigation, irrigation fluid will be supplied to the connector 29, and then through the passageway 42 and through the connecting passage 60 to the interior of the irrigation needle 46. The fluid will flow within the irrigation needle 46 and outside the aspiration needle 49, and will be dispensed from the irrigation openings 50.

When a piece of tissue is within the aspiration port 61 and it is desired to cut that piece of tissue, the appropriate controls will be manipulated to cause fluid pressure to be applied on the connector 28 which will cause the cylinder 31 to project its rod 32 and move the driving device 36 forwardly in the barrel 25. During the forward movement, the interaction of the grooves 39 with the ridges 40 will cause the driving device 36 to rotate. Since the cutting device 66 is connected to the driving device 36, the cutting device 66 will also be caused to rotate and to move forwardly within the aspiration needle 49. It will be understood that the dimensions are such that the cutting end 68 of the cutting device 66 will extend across the aspiration port 61 to sever any material extending therethrough. The rotation of the cutting edge 68 provides for easier cutting of any tissue extending through the aspiration port 61 so that the tissue is cut more easily and with less trauma to the patient. Once the cutting device 66 has moved to its forwardmost point of travel, pressure would be removed from connector 28 and the spring 41 would urge the driving device 36 rearwardly to urge the rod 32 back into the cylinder 31. Of course, if the tissue is not severed on the first effort, pressure would be again applied to the connector 28 and the process would be repeated.

In the event a piece of tissue inadvertently extends into the aspiration port 61 and the tissue is not to be severed, the surgeon can operate the appropriate controls to stop the aspiration at the connector 16 and to release the tubing clamp 21 to provide reflux irrigation through the line 19 and to the connector 16. This would provide for liquid through the passageway 44 and ultimately into the aspiration needle 49 so that there would be a combination of cessation of vacuum and positive irrigation to remove tissue from the aspiration port 61. This allows a very gentle removal of the tissue without trauma to the patient. Once the tissue has been removed from the aspiration port 61 and the procedure is to be continued, the operating device 22 would be operated to close the tubing clamp 21 and prevent further irrigation through the line 19, and the controls would be operated to connect the vacuum to the connector 16 to continue aspiration as normal.

It will therefore be seen that present invention provides a very simple handpiece for use in ophthamic procedures, the handpiece allowing simultaneous aspiration and irrigation, and further providing for a rotating cutting means for cutting tissue extending through the aspiration port of the aspiration needle. The device is extremely simple and reliable, and it is designed for easy replacement of the various needles involved, including the cutting device.

It will of course be understood by those skilled in the art that the particular embodiment of the invention here presented is by way of illustration only, and is meant to be in no way restrictive; therefore, numerous changes and modifications may be made, and the full use of equivalents resorted to without departing from the spirit or scope of the invention as defined in the appended claims.

I claim:

1. A pneumatic surgical instrument for use in ophthalmic surgery comprising;
   a handpiece having a body and a needle extending from said body,
   said needle including an aspiration port in communication with an aspiration passage coaxial therewith, and a cutting device, rotable and reciprocable within said aspiration passage, said cutting device being movable across said aspiration port for severing tissue extending therethrough,
   said needle further including an irrigation needle coaxial therewith and terminating short of said aspiration port, said body defining a first bore therein and a second bore coaxial with said first bore,
   a driving device within said first bore and reciprocable therein, said driving device having said cutting device fixed thereto for movement therewith,
   fluid operated means for causing said driving device to move in a first direction, said fluid operated means comprising a pneumatic cylinder having a rod projecting therefrom toward the driving device, said rod being arranged to engage said driving device on projection from said pneumatic cylinder,
   resilient means to cause said driving device to move in the opposite direction, and
   helical means on said driving device for causing rotation of said driving device about its axis as said driving device moves in said first bore.

2. A surgical instrument as claimed in claim 1 wherein said body defining an aspiration passageway therethrough communicating with said first bore, a Y connector communicating with said aspiration passageway, aspiration means connected to one branch of said Y connector, and reflux irrigation means connected to the other branch of said Y connector.

3. A surgical instrument as claimed in claim 1 wherein said irrigation needle being releasably received on said body, said aspiration passage being defined within an aspiration needle coaxially disposed with respect to said irrigation needle, said aspiration needle being releasably fixed to said body, and said cutting device being releasably fixed to said driving device.

4. A surgical instrument as claimed in claim 3 wherein said body defines an irrigation passageway therethrough, said irrigation passageway being in communication with said irrigation needle, and irrigation means for supplying irrigation fluid to said irrigation passageway.

5. A surgical instrument as claimed in claim 1 wherein said resilient means comprises a spring surrounding said cutting device and engaging said driving device for urging said driving device rearwardly.

* * * * *